United States Patent
Lee et al.

(10) Patent No.: US 12,371,664 B2
(45) Date of Patent: Jul. 29, 2025

(54) MEDIUM FOR DIRECT DIFFERENTIATION OF PLURIPOTENT STEM CELL-DERIVED MESENCHYMAL STEM CELL, METHOD FOR PREPARING MESENCHYMAL STEM CELL BY USING SAME, AND MESENCHYMAL STEM CELL PREPARED THEREBY

(71) Applicant: CHA BIOTECH CO., LTD., Seoul (KR)

(72) Inventors: Dong Ryul Lee, Seoul (KR); Jeong Eun Lee, Seoul (KR); Soo Kyung Jung, Gwangju-si (KR); Kyung Soon Park, Seongnam-si (KR); Ji Hoon Park, Suwon-si (KR)

(73) Assignee: CHA BIOTECH CO., LTD., Seoul (KR)

( * ) Notice: Subject to any disclaimer, the term of this patent is extended or adjusted under 35 U.S.C. 154(b) by 1172 days.

(21) Appl. No.: 17/274,029

(22) PCT Filed: Sep. 6, 2019

(86) PCT No.: PCT/KR2019/011529
§ 371 (c)(1),
(2) Date: Mar. 5, 2021

(87) PCT Pub. No.: WO2020/050673
PCT Pub. Date: Mar. 12, 2020

(65) Prior Publication Data
US 2021/0340498 A1    Nov. 4, 2021

(30) Foreign Application Priority Data
Sep. 7, 2018    (KR) .................. 10-2018-0107385

(51) Int. Cl.
*C12N 5/0775* (2010.01)
*A61K 35/28* (2015.01)

(52) U.S. Cl.
CPC ............ *C12N 5/0668* (2013.01); *A61K 35/28* (2013.01); *C12N 2500/30* (2013.01);
(Continued)

(58) Field of Classification Search
CPC ............ C12N 5/0668; C12N 2500/30; C12N 2501/734; C12N 2527/00; C12N 2533/00;
(Continued)

(56) References Cited

U.S. PATENT DOCUMENTS

| | | |
|---|---|---|
| 10,011,819 B2 | 7/2018 | Pan et al. |
| 2010/0166713 A1* | 7/2010 | Dalton ................. C12N 5/0606 435/363 |
| 2017/0275593 A1 | 9/2017 | Hanna et al. |

FOREIGN PATENT DOCUMENTS

| | | | | |
|---|---|---|---|---|
| AU | 2014203737 A1 * | 7/2014 | ........... | C12N 5/0603 |
| JP | 2014-239676 A | 12/2014 | | |

(Continued)

OTHER PUBLICATIONS

Molandado et al. Rock inhibitor primes human induced pluripotent stem cells to selectively differentiate towards mesendodermal lineage via epithelial-mesenchymal transition-like modulation. Stem Cell Res. Sep. 2016;17(2):222-227. (Year: 2016).*

(Continued)

*Primary Examiner* — Marcia S Noble
*Assistant Examiner* — Briana N Ebbinghaus
(74) *Attorney, Agent, or Firm* — Oblon, McClelland, Maier & Neustadt, L.L.P.

(57) ABSTRACT

A medium for direct differentiation of embryonic stem cell-derived mesenchymal stem cells, a method of preparing mesenchymal stem cells by using the same, mesenchymal (Continued)

stem cells prepared thereby, and a cell therapy product comprising the same mesenchymal stem cells. In a medium composition and in a method according to an embodiments, mesenchymal stem cells may be prepared at high yield within a short period of time. In addition, the method is simple in preparation procedure because of the absence of an embryoid body formation step that allows homogeneous cells to be prepared, thus advantageously providing a cell therapy product within a reduced period of time, compared to conventional methods.

13 Claims, 10 Drawing Sheets

(52) U.S. Cl.
    CPC .... *C12N 2501/734* (2013.01); *C12N 2527/00* (2013.01); *C12N 2533/00* (2013.01)
(58) Field of Classification Search
    CPC .......... C12N 2501/115; C12N 2501/15; C12N 2501/727; C12N 2501/73; C12N 2502/1323; C12N 2506/02; C12N 2513/00; C12N 5/0662; C12N 2500/32; C12N 2506/45; A61K 35/28
    See application file for complete search history.

(56) References Cited

FOREIGN PATENT DOCUMENTS

| | | | |
|---|---|---|---|
| JP | 2015-509719 | A | 4/2015 |
| JP | 2018-531027 | A | 10/2018 |
| KR | 10-2010-0138023 | A | 12/2010 |
| KR | 10-2012-0126236 | A | 11/2012 |
| KR | 10-2013-0118674 | A | 10/2013 |
| KR | 10-2014-0138221 | A | 12/2014 |
| WO | WO 2012/087965 | A2 | 6/2012 |

OTHER PUBLICATIONS

Huang et al. Targeting the homologous recombination pathway by small molecule modulators. Bioorg Med Chem Lett. Jul. 15, 2014;24(14):3006-13. (Year: 2014).*
Hynes et al. Generation of Functional Mesenchymal Stem Cells from Different Induced Pluripotent Stem Cell Lines. Stem Cells Dev. May 15, 2014; 23(10): 1084-1096. (Year: 2014).*
Oswald et al. Mesenchymal Stem Cells Can Be Differentiated Into Endothelial Cells In Vitro. Stem Cells. 2004;22(3):377-84. (Year: 2004).*
Maldonado et al. Rock inhibitor primes human induced pluripotent stem cells to selectively differentiate towards mesendodermal lineage via epithelial-mesenchymal transition-like modulation. Stem Cell Res. Sep. 2016;17(2):222-227. (Year: 2016).*
Song et al. RS-1 enhances CRISPR/Cas9- and TALEN-mediated knock-in efficiency. Nat Commun. Jan. 28, 2016:7:10548. (Year: 2016).*
Marion et al. Mesenchymal Stem Cells and Tissue Engineering. Methods Enzymol. 2006:420:339-61. (Year: 2006).*
Lu et al. Generation of functional hemangioblasts from human embryonic stem cells. Nat Methods. Jun. 2007;4(6):501-9. (Year: 2007).*
Kimbrel et al. Mesenchymal Stem Cell Population Derived from Human Pluripotent Stem Cells Displays Potent Immunomodulatory and Therapeutic Properties. Stem Cells Dev. Jul. 15, 2014;23(14):1611-24. (Year: 2014).*
Cooper GM. The Cell: A Molecular Approach. 2nd edition. Sunderland (MA): Sinauer Associates; 2000. (Year: 2000).*
Yang et al. Glycogen synthase kinase 3b inhibition enhances repair of DNA double-strand breaks in irradiated hippocampal neurons. Neuro Oncol. May 2011;13(5):459-70. (Year: 2011).*
Exfoliated. Cambridge Dictionary (accessed at https://dictionary.cambridge.org/us/dictionary/english/exfoliated on Jun. 13, 2024) (Year: 2024).*
Wu et al. Reversible transition between hepatocytes and liver progenitors for in vitro hepatocyte expansion. Cell Res. May 2017;27(5):709-712. Epub Apr. 4, 2017. (Year: 2017).*
Examination report as received in the AU patent application No. 2019334666, dated Nov. 11, 2022, 3 pages, citing documents 24 and 25.
Laura Sánchez et al: "Enrichment of Human ESC-Derived Multipotent Mesenchymal Stem Cells with Immunosuppressive and Anti-Inflammatory Properties Capable to Protect Against Experimental Inflammatory Bowel Disease", Stem Cells, vol. 29, No. 2, Feb. 1, 2011 (Feb. 1, 2011), pp. 251-262, XP055080564, ISSN: 1066-5099, DOI: 10.1002/stem.569.
Barberi T et al: "Derivation of multipotent mesenchymal precursors from human embryonic stem cells", PLOS Medicine, Public Library of Science, US, vol. 2, No. 6, Jun. 1, 2005 (Jun. 1, 2005), pp. 554-560, XP002544487, ISSN: 1549-1676, [retrieved on 20050628], DOI: 10.1371/JOURNAL.PMED.0020161.
Examination report as received in the AU patent application No. 2019334666, dated Jun. 13, 2023, 3 pages.
Notice of Acceptance for Patent Application as received in the AU patent application No. 2019334666, dated Oct. 20, 2023, 3 pages.
Jung Soo Kyung et al: "Rapid production and genetic stability of human mesenchymal progenitor cells derived from human somatic cell nuclear transfer-derived pluripotent stem cells" International Journal of Molecular Sciences, vol. 22, No. 17, Aug. 26, 2021 (Aug. 26, 2021), 17 pages, XP 055921750.
Jung S et al: "42 gene expression profiling and genetic stability of human somatic cell nuclear transfer embryonic stem cell-derived mesenchymal progenitor cells produced by two different protools" Cytotherapy, May 1, 2020 (May 1, 2020), 5 pages.
Choi Eui-Hwan et al: "Combined ectopic Expression of Homologus recombination factors promotes embryonic stem cell differentiation" Molecular Therapy, vol. 26, No. 4, Apr. 1, 2018 (Apr. 1, 2018), 12 pages.
Japanese Office Action issued on May 31, 2022, in the JP patent Application No. 2021-512726, 5 pages.
Flamant S et al: "41 human induced pluripotent stem cells as source of mesenchymal stromal cells for the treatment of cutaneous radiation injuries" May 1, 2020 (May 1, 2020), 3 pages.
European Office Action issued on May 27, 2022, in European Patent Application No. 19858301.5, 5 pages, citing documents 1, 15-16, 24-25, 28-30 and 32.
Chow, L. et al., "Safety and immune regulatory properties of canine induced pluripotent stem cell-derived mesenchymal stem cells," Stem Cell Research, 2017, vol. 25, pp. 221-232.
Choi, E.H. et al., "Combine Ectopic Expression of Homologous Recombination Factors Promotes Embryonic Stem Cell Differentiation," Molecular Therapy, vol. 26, No. 4, Apr. 2018, pp. 1154-1165.
Song, J. et al., "RS-1 enhances CRISPR/Cas9- and TALEN-mediated knock-in efficiency," Nature Communications, Jan. 28, 2016, vol. 7, Article No. 10548, pp. 1-7.
Sherman, M.H. et al., "Regulation of cell differentiation by the DNA damage response," Trends in cell biology, May 2011, vol. 21, No. 5, pp. 312-319.
Office Action issued on Jul. 15, 2020 in Korean Application No. 10-2019-0110785, citing document AS therein, 4 pages.
Office Action issued on Feb. 26, 2021 in Korean Application No. 10-2019-0110785, citing documents AS-AU therein, 5 pages.
International Search Report issued on Dec. 17, 2019 in PCT/KR2019/011529 filed on Sep. 6, 2019, citing documents AA, AN-AQ and AU-AV therein, 2 pages.
Office Action issued Aug. 20, 2024, in corresponding Japanese Patent Application No. 2023-045082, 3 pages.

* cited by examiner

MEDIUM FOR DIRECT DIFFERENTIATION OF PLURIPOTENT STEM CELL-DERIVED MESENCHYMAL STEM CELL, METHOD FOR PREPARING MESENCHYMAL STEM CELL BY USING SAME, AND MESENCHYMAL STEM CELL PREPARED THEREBY

TECHNICAL FIELD

The present disclosure relates to a medium for direct differentiation of pluripotent stem cell-derived, e.g., embryonic stem cell-derived mesenchymal stem cells, a method of preparing mesenchymal stem cells by using the same, mesenchymal stem cells prepared thereby, and a cell therapy product including the same.

BACKGROUND ART

As a conventional method of preparing mesenchymal stem cell using human embryonic stem cells, a method of preparing mesenchymal stem cell by forming an embryoid body and treating with a TGF-β inhibitor for 14 days has been reported. The TGF-β inhibitor is used to easily obtain mesodermal cells by inhibiting differentiation of the embryoid body into endodermal cells. In addition, SB431542, as a TGF-β inhibitor, used in the preparation of mesenchymal stem cells using human embryonic stem cells is used in an amount of 10 μM or more. Among the TGF-β inhibitors, 1 μM or more of SB431542 has effects on inhibiting the activity of a transcription factor required for endodermal differentiation and increasing the activity of a transcription factor required for mesodermal differentiation. In addition, although there are cases in which differentiation is induced by treatment with SB431542, one of the TGF-β inhibitors, in direct differentiation methods not via embryoid body, it has been reported that a long treatment period of 11 days or more is required at a high concentration of 10 μM or more. Therefore, a long time is taken for mesenchymal stem cells prepared according to the previously reported method to exhibit high mesodermal properties. In addition, although embryoid bodies having uniform size and shape are formed and used, technical instability may affect differentiation efficiency and properties of differentiated cells since effects of a drug are not uniform due to difference in microenvironment in cells constituting the inside and outside of the embryoid bodies.

Therefore, although biological therapeutic agents are prepared based on proliferation of cells, any actions to prevent or compensate for the risk of cellular senescence and mutation that might be caused during proliferation have not been taken in the preparation of the therapeutic agent. Thus, there is a need to develop technology to solve this problem.

DESCRIPTION OF EMBODIMENTS

Technical Problem

Provided is a medium composition for inducing differentiation of pluripotent stem cells into mesenchymal stem cells including a DNA repair agent and a Rho-associated, coiled-coil containing protein kinase (ROCK) inhibitor.

Provided also is a use of a DNA repair agent and a Rho-associated, coiled-coil containing protein kinase (ROCK) inhibitor for preparation of a medium composition for inducing differentiation of pluripotent stem cells into mesenchymal stem cells.

Provided also is a method of preparing pluripotent stem cell-derived mesenchymal stem cells including: culturing isolated pluripotent stem cells; and inducing differentiation of the cultured pluripotent stem cells into mesenchymal stem cells by culturing the pluripotent stem cells in a medium including a DNA repair agent and a Rho-associated, coiled-coil containing protein kinase (ROCK) inhibitor.

Provided also are pluripotent stem cell-derived mesenchymal stem cells differentiation-induced in the presence of a DNA repair agent and a Rho-associated, coiled-coil containing protein kinase (ROCK) inhibitor.

Provided also is a cell therapy product including the pluripotent stem cell-derived mesenchymal stem cells.

Provided also is a use of the pluripotent stem cell-derived mesenchymal stem cells for preparation of the cell therapy product.

Provided also is a method of treating a disease including administering the pluripotent stem cell-derived mesenchymal stem cells into an individual.

Solution to Problem

According to an aspect of the present disclosure, a medium composition for inducing differentiation of pluripotent stem cells into mesenchymal stem cells includes a DNA repair agent and a Rho-associated, coiled-coil containing protein kinase (ROCK) inhibitor.

According to another aspect of the present disclosure, a use of a DNA repair agent and a Rho-associated, coiled-coil containing protein kinase (ROCK) inhibitor is for preparation of a medium composition for inducing differentiation of pluripotent stem cells into mesenchymal stem cells.

Throughout the specification, the term "pluripotent stem cell" refers to a cell having a capacity for self-renewal (the ability of passing through a number of cell division cycles while maintaining an undifferentiated state thereof) and a cell having a multi-differentiation potential into one or more cells (the ability to differentiate into one or more specialized cells). Mesenchymal stem cell (MSC) is a stem cell having multipotency capable of differentiating into a variety of mesodermal cells such as osteoblasts, chondrocytes, adipocytes, and myocytes or ectodermal cells such as neuronal cells. The pluripotent stem cells may be nuclear transfer pluripotent stem cells (NT-hPSC), parthenote-derived human pluripotent stem cells (pn-hPSC), induced pluripotent stem cells (iPSC), or embryonic stem cells (ESC).

In the present disclosure, "somatic cell" refers to any cell in tissue in a living body other than a gamete or a progenitor cell thereof.

As used herein, the "maturation" refers to a process of harmonized biochemical steps leading to a finally differentiated cell type.

Throughout the specification, the "differentiation" refers to adaptation of a cell to a particular form or function.

Throughout the specification, the "differentiated cell" includes any somatic cell that is not multipotent as defined herein. Thus, the term "differentiated cell" also includes partially differentiated cell, e.g., multipotent cell, or a stable, non-pluripotent partially reprogrammed or partially differentiated cell produced using any composition and method described herein. In some embodiments, the differentiated cell is a stable intermediate cell, such as non-pluripotent, partially reprogrammed cell. It may be understood that placing many primary cells in culture may lead to some loss of fully differentiated characteristics. Thus, simply culturing such differentiated or somatic cells does not turn these cells into non-differentiated cells (e.g., undifferentiated cells) or pluripotent cells. Transition of differentiated cells (including a stable, non-pluripotent, partially reprogrammed cell intermediate) into pluripotent cells requires a reprogramming stimulus beyond the stimuli that lead to some loss of differentiated characteristics upon placement in culture. Reprogramed, in some embodiments, partially reprogrammed cells, also have the characteristic of having the capacity to undergo extended passages without loss of growth potential, relative to parental cells having lower developmental potential, which generally have capacity for only a limited number of divisions in culture. In some embodiments, the term "differentiated cell" also refers to a cell of a more specialized cell type (i.e., decreased developmental potential) derived from a cell of a less specialized cell type (i.e., increased developmental potential) (e.g., from an undifferentiated cell or a reprogrammed cell) where the cell has undergone a cellular differentiation process. More particularly, the differentiated cells may be selected from hematopoietic stem cells, myocytes, cardiomyocytes, hepatocytes, chondrocytes, epithelial cells, urinary cells, adipocytes, renal cells, vascular cells, retinal cells, mesenchymal stem cells (MSC), and neuronal cells in the specification.

In an embodiment, the DNA repair agent may be a substance that increases the activity of Rad51 (Rad51 activator). The Rad51 activator may be 3-[(benzylamino)sulfonyl]-4-bromo-N-(4-bromophenyl)benzamide or 4-bromo-N-(4-bromophenyl)-3-[[(phenylmethyl)amino]sulfonyl]-benzamide. The DNA repair agent may be contained in a concentration of 5 μM to 25 μM, 5 μM to 20 μM, 6 μM to 18 μM, 8 μM to 15 μM, or 8 μM to 12 μM. The RAD51 activator may maintain the DNA repairing effect by increasing the activity of a RAD51 protein by maintaining binding stability of the RAD51 protein having the function of repairing damaged DNA to single strand DNA (ssDNA) or double strand DNA (dsDNA). Thus, without being limited to a specific theory, a cell therapy product with genetic safety may be prepared via treatment with the RAD51 activator in differentiation of pluripotent stem cells into mesodermal stem cells to decrease the probability of mutation and caused by cell proliferation and repeated subculturing and to delay occurrence of cellular senescence caused thereby.

In an embodiment, the ROCK inhibitor may be one selected from Fasudil, Ripasudil, 4-((R)-1-aminoethyl)-N-(pyridin-4-yl)cyclohexanecarboxamide, 4-(1-aminoethyl)-N-(1H-pyrrolo(2,3-b)pyridin-4-yl)cyclohexanecarboxamide dihydrochloride, N-(6-fluoro-1H-indazol-5-yl)-1,4,5,6-tetrahydro-2-methyl-6-oxo-4-[4-(trifluoromethyl)phenyl]-3-pyridinecarboxamide, 1-(3-hydroxybenzyl)-3-[4-(pyridin-4-yl)thiazol-2-yl]urea, 2-methyl-1-[(4-methyl-5-isoquinolinyl)sulfonyl]-hexahydro-1H-1,4-diazepine dihydrochloride, N-[2-[2-(dimethylamino)ethoxy]-4-(1H-pyrazol-4-yl)phenyl-2,3-dihydro-1,4-benzodioxin-2-carboxamide dihydrochloride], 2-fluoro-N-[[4-(1H-pyrrolo[2,3b]-pyridin-4-yl)phenyl]methyl]benzenemethanamine dihydrochloride, N-[3-[[2-(4-amino-1,2,5-oxadiazol-3-yl)-1-ethyl-1H-imidazo[4,5-c]pyridin-6-yl]oxy]phenyl]-4-[2-(4-morpholinyl)ethoxy]benzamide, (3S)-1-[[2-(4-amino-1,2,5-oxadiazol-3-yl)-1-ethyl-1H-imidazo[4,5-c]pyridin-7-yl]carbonyl]-3-pyrrolidinamine dihydrochloride, N-[(1S)-2-hydroxy-1-phenylethyl]-N'-[4-(4-pyridinyl)phenyl]-urea, Azaindole-1, and Narciclasine. The ROCK inhibitor may be contained in a concentration of 5 μM to 25 μM, 5 μM to 20 μM, 6 μM to 18 μM, 8 μM to 15 μM, or 8 μM to 12 μM. In development of the cell therapy product, the functions of the ROCK inhibitor involve intermediate filament disruption by molecular biologically active RHO protein, actin-membrane linkage, apoptosis mechanism activation, and inhibition of expression of cellular senescence-associated markers P16 and P21 which may be caused by repeated subculturing. Based on these functions, the ROCK inhibitor has inhibitory effects on increases in stress in cells and delaying effects on cellular senescence which may be caused by rapid metabolic changes during cell differentiation. Thus, without being limited to a specific theory, stability and efficiency of differentiation into mesenchymal stem cells may be improved by re-adjusting an appropriate treatment amount and a treatment period of the ROCK inhibitor.

In an embodiment, the medium composition may further include a TGF-β inhibitor. The TGF-β inhibitor may be one selected from 4-{4-[3-(pyridin-2-yl)-1H-pyrazol-4-yl]-pyridin-2-yl}-N-(tetrahydro-2H-pyran-4-yl)benzamide hydrate, 4-[3-(2-pyridinyl)-1H-pyrazol-4-yl]-quinoline, 2-[3-(6-methyl-2-pyridinyl)-1H-pyrazol-4-yl]-1,5-naphthyridine, 4-(5-benzol[1,3]dioxol-5-yl-4-pyridin-2-yl-1H-imidazol-2-yl)-benzamide hydrate, 4-[4-(1,3-benzodioxol-5-yl)-5-(2-pyridinyl)-1H-imidazol-2-yl]-benzamide hydrate, 4-[4-(3,4-methylenedioxyphenyl)-5-(2-pyridyl)-1H-imidazol-2-yl]-benzamide hydrate, 3-(6-methyl-2-pyridinyl)-N-phenyl-4-(4-quinolinyl)-1H-pyrazole-1-carbothioamide, 2-(3-(6-methylpyridine-2-yl)-1H-pyrazol-4-yl)-1,5-naphthyridine, 4-[3-(2-pyridinyl)-1H-pyrazol-4-yl]-quinoline, 2-[4-(1,3-benzodioxol-5-yl)-2-(1,1-dimethylethyl)-1H-imidazol-5-yl]-6-methyl-pyridine, 2-(5-chloro-2-fluorophenyl)-4-[(4-pyridyl)amino]pteridine, 6-[2-tert-butyl-5-(6-methyl-pyridin-2-yl)-1H-imidazol-4-yl]-quinoxaline, 4-{4-[3-(pyridin-2-yl)-1H-pyrazol-4-yl]pyridin-2-yl}-N-(tetrahydro-2H-pyran-4-yl)benzamide hydrate, 4-[2-fluoro-5-[3-(6-methyl-2-pyridinyl)-1H-pyrazol-4-yl]phenyl]-1H-pyrazole-1-ethanol, and 3-[[5-(6-methyl-2-pyridinyl)-4-(6-quinoxalinyl)-1H-imidazol-2-yl]methyl]benzamide. The TGF-β inhibitor may be contained in a concentration of 0.2 μM to 2.0 μM, 0.2 μM to 1.6 μM, 0.4 μM to 1.6 μM, 0.6 μM to 1.4 μM, 0.8 μM to 1.2 μM, or 0.6 μM to 1.0 μM. In an embodiment, when the medium composition is used, the TGF-β inhibitor may be used at a significantly lower concentration than that of the TGF-β inhibitor used in conventional approaches reported in the related art, and thus side effects caused by a high concentration of the TGF-β inhibitor may be reduced and mesodermal stem cells may be obtained at a high yield even by using the TGF-β inhibitor at a low concentration.

The medium may be selected from Minimal Essential Medium (MEM), Dulbecco modified Eagle Medium (DMEM), Roswell Park Memorial Institute Medium (RPMI), Keratinocyte Serum Free Medium (K-SFM), Iscove's Modified Dulbecco's Medium (IMDM), F12, and DMEM/F12.

Also, the medium may include a neutral buffer (e.g., phosphate and/or high-concentration bicarbonate) and protein nutrients (e.g., serum, such as FBS, fetal calf serum (FCS), horse serum, serum replacement, and albumin, or essential amino acid and non-essential amino acid such as glutamine and L-glutamine) in an isotonic solution. The medium may further include a lipid (e.g., fatty acid, cholesterol, and HDL or LDL extract of serum) and other components found in most preservative media of this type (e.g., transferrin, nucleoside or nucleotide, pyruvate, sugar source in any ionized form or salt such as glucose, glucocorticoid such as hydrocortisone, and/or a reducing agent such as β-mercaptoethanol).

Also, the medium may advantageously include an anti-clumping agent, such as products purchased from Invitrogen (Cat #0010057AE) to prevent cells from adhering to each other, adhering to a container wall, or forming too large clumps.

Among them, the medium may further include at least one additive selected from the following products:

a stem cell factor (SCF, steel factor), other ligands or antibodies for c-kit dimerization, and other activators of the same signal transduction pathway; other tyrosine kinase-associated receptors such as platelet-derived growth factor (PDGF), macrophage colony-stimulating factor, Flt-3 ligand and ligand for vascular endothelial growth factor (VEGF) receptor; a factor raising cyclic AMP levels such as forskolin; a factor inducing gp130 such as LIF or Oncostatin-M; a hematopoietic growth factor such as thrombopoietin (TPO); a transforming growth factor such as TGF β1; a neurotrophin such as CNTF; and an antibiotic such as gentamicin, penicillin, and streptomycin.

The medium composition according to an embodiment may further include at least one component selected from the group consisting of fetal bovine serum (FBS), N-acetyl-L-cysteine (NAC), non-essential amino acid (NEAA), fibroblast growth factor (FGF), insulin or insulin-like factor, hydrocortisone, dexamethasone, basic fibroblast growth factor (bFGF), heparan sulfate, 2-mercaptoethanol, and epidermal growth factor (EGF), in addition to the above-described components.

The medium composition according to an embodiment may be used to induce differentiation of pluripotent stem cells into mesenchymal stem cells. Specifically, the medium composition may be used after differentiation of the cultured pluripotent stem cells into mesodermal cells (for example, treatment with TGF-β inhibitor), before mature differentiation of the mesodermal cells into mesenchymal stem cells. Thus, the medium composition may be used for pretreatment of immature mesenchymal stem cells (mesodermal cells) before mature differentiation of the mesenchymal stem cells.

In addition, the medium composition according to an embodiment may be a medium composition for inducing direct differentiation.

As used herein, the term "direct differentiation" refers to differentiation of pluripotent stem cells directly into final mesenchymal stem cells, not via hamangioblasts, but via immature mesenchymal stem cells having characteristics of hematopoietic stem cells, without forming an embryoid body, in the differentiation of pluripotent stem cells into mesenchymal stem cells.

According to another aspect of the present disclosure, a method of preparing pluripotent stem cell-derived mesenchymal stem cells includes: culturing isolated pluripotent stem cells; and inducing differentiation of the cultured pluripotent stem cells into mesenchymal stem cells by culturing the pluripotent stem cells in a medium including a DNA repair agent and a Rho-associated, coiled-coil containing protein kinase (ROCK) inhibitor.

Specifically, the method may include: culturing the isolated pluripotent stem cells; differentiating the cultured pluripotent stem cells into mesodermal cells (for example, in the presence of a TGF-β inhibitor); inducing differentiation of the mesodermal cells into mesenchymal stem cells by culturing the mesodermal cells in a medium including a DNA repair agent and a Rho-associated, coiled-coil containing protein kinase (ROCK) inhibitor (interchangeably used with "pre-treating in a medium" or "preparing immature mesenchymal stem cells by culturing in a medium"); culturing the differentiation-induced mesenchymal stem cells in a mesenchymal stem cell maturation medium; and/or subculturing the mesenchymal stem cells cultured in the maturation medium.

In another embodiment, the method may not substantially include a process of forming an embryoid body formation step.

The culturing of isolated pluripotent stem cells may be performed in the absence of feeder cells. In addition, the culturing may be performed in a culture dish coated with a cell adhesion enhancer (e.g., CTS Cellstart™). The culturing may be performed in a stem cell conditioned medium (e.g., mTeSR™) for about 1 day to 10 days or for about 3 days to 10 days.

The differentiating into the mesodermal cells may be performed in the presence of the TGF-β inhibitor. In an embodiment, the differentiating may include culturing the cells in a medium containing the TGF-β inhibitor for 1 day to 8 days, 2 days to 7 days, 2 days to 6 days, or 2 days to 4 days. When the culturing is maintained for 7 days or more, cellular senescence may occur, morphological characteristics of cells may be changed, or proliferation ability of cells may deteriorate. In terms of the cellular senescence, morphological characteristics, or proliferation ability, the culturing may be performed for 2 days to 6 days. The medium may be selected from Minimal Essential Medium (MEM), Dulbecco modified Eagle Medium (DMEM), Roswell Park Memorial Institute Medium (RPMI), Keratinocyte Serum Free Medium (K-SFM), Iscove's Modified Dulbecco's Medium (IMDM), F12, and DMEM/F12. In addition, the medium may further include additional compounds described herein.

The inducing of differentiation of the cultured mesodermal cells into mesenchymal stem cells by culturing the mesodermal cells in a medium including a DNA repair agent and a Rho-associated, coiled-coil containing protein kinase (ROCK) inhibitor may mean a pretreatment stage before mature differentiation of mesenchymal stem cells or a stage of inducing differentiation into immature mesenchymal stem cells. The medium is as described above. The culturing may include inducing differentiation in a medium including the DNA repair agent, the ROCK inhibitor, and/or the TGF-β inhibitor for 1 day to 4 days or 1 day to 2 days. In the step of inducing differentiation into the mesenchymal stem cells, the mesenchymal stem cells may be immature mesenchymal stem cells. Thus, according to the method according to an embodiment, the mesenchymal stem cells may be prepared via the immature mesenchymal stem cells. Specifically, according to the method according to an embodiment, mesenchymal stem cells may be prepared not via hamangioblasts, but via immature mesenchymal stem cells. Because 10% or less of the immature mesenchymal stem cells in the population are positive for VEGFR2 that is a marker of hemangioblasts, it is confirmed that the method according to an embodiment is performed not via the hemangioblasts.

The culturing of the differentiation-induced mesenchymal stem cells in a mesenchymal stem cell maturation medium may include: preparing a single cell suspension by treating the mesenchymal stem cells with trypsin (trypsin/EDTA solution); culturing the cells in a mesenchymal stem cell maturation medium; centrifuging the cells cultured in the maturation medium, and/or subculturing the mesenchymal stem cells cultured in the maturation medium. The culturing in the maturation medium may be performed for 1 day to 15 days, 1 day to 12 days, or 4 days to 12 days. Also, the maturation medium may be selected from Minimal Essential Medium (MEM), Dulbecco modified Eagle Medium (DMEM), Roswell Park Memorial Institute Medium (RPMI), Keratinocyte Serum Free Medium (K-SFM), Iscove's Modified Dulbecco's Medium (IMDM), F12, and DMEM/F12. In addition, the medium may further include additional compounds described herein. After the centrifuging, the cells obtained by centrifuging may be subcultured. The subculturing may be performed in a medium similar or identical to the maturation medium. In addition, the subculturing may be performed by preparing a single cell suspension in the presence of trypsin (e.g., trypsin/EDTA solution). Also, the subculturing may be performed in a culture dish coated with a cell adhesion enhancer. In the specification, the "subculturing" may refer to a method of continuously culturing cells in a healthy state for a long period of time over generations by periodically transferring some cells to a new culture dish and culturing the cells with a fresh culture medium. As the number of cells increases in a culture dish with a limited space, nutrients for proliferation are consumed or toxic metabolites accumulate after a certain period of time resulting in natural cell death. Thus, subculturing is used to increase the number of healthy cells and one replacement of the medium (culture dish) or one division of the group of cells into new fresh culture mediums is generally referred to as 1 passage. The subculturing may be performed using any known method without limitation, for example, by mechanical separation or enzymatic separation. The subculturing may be performed from 1 passage to 20 passages, 3 passages to 20 passages, or 3 passages to 15 passages. Also, the method may further include removing non-mesodermal stem cells exfoliated during the subculturing and isolating mesenchymal stem cells. Through the subculturing, final mesenchymal stem cells may be prepared.

According to another aspect of the present disclosure, mesenchymal stem cells are prepared by the above-described method.

In an embodiment, the mesenchymal stem cells may be pluripotent stem cell-derived mesenchymal stem cells differentiation-induced in the presence of a DNA repair agent and a Rho-associated, coiled-coil containing protein kinase (ROCK) inhibitor.

With regard to markers expressed on cell surfaces, about 20%, about 25%, about 30%, about 35%, about 40%, about 45%, about 50%, about 55%, about 60%, about 65%, about 70%, about 75%, about 80%, about 85%, about 90%, about 95%, about 98%, or about 99% or more of the pluripotent stem cell-derived mesenchymal stem cells provided in the present disclosure may be positive for CD29, CD44, CD90, or CD105 surface marker and at least 70% or less, at least 60% or less, at least 50% or less, at least 40% or less, at least 30% or less, at least 20% or less, at least 10% or less, at least 5% or less, or at least 1% or less of the cells are negative for TRA-160, CD34, or VEFGR2 surface marker. In the present disclosure, the term "positive", with respect to a stem cell marker, may mean that the marker is present in a large amount or a high concentration, as compared with that in other non-stem cells used as a reference. That is, because a marker is present inside or on the surface of a cell, the cell is positive for the marker when the cell is distinguished from one or more cell types by using the marker. Furthermore, the positive may mean that the cell has signals of higher intensity than a background intensity, for example, a cell has the marker in an amount enough to be detectable by a cell measurement device. For example, when a cell may be detectable by a CD29-specific antibody and signals from the antibody are detectably stronger than those of a control (e.g., background intensity), the cell is "CD29+". In the present disclosure, the term "negative" means that a marker cannot be detected as compared with the background intensity although an antibody specific to the surface marker of a certain cell is used. For example, when a cell cannot be detectably labeled with a CD34-specific antibody, the cell is "CD34−".

The immunological characteristics may be determined by any methods well known in the art to which the present disclosure pertains. For example, various methods such as flow cytometry, immunohistochemical staining, RT-PCR, or the like may be used.

In addition, the mesenchymal stem cells may have the ability to differentiate into at least one selected from hematopoietic stem cells, myocytes, cardiomyocytes, hepatocytes, chondrocytes, epithelial cells, urinary cells, renal cells, vascular cells, retinal cells, and neuronal cells.

According to another aspect of the present disclosure, a population of mesenchymal stem cells is prepared according to the above-described method.

According to another aspect of the present disclosure, a cell therapy product, a pharmaceutical composition, or a preparation includes mesenchymal stem cells, a population thereof, or a culture solution thereof prepared according to the above-described method, as an active ingredient.

According to another aspect of the present disclosure, a use of mesenchymal stem cells, a population thereof, or a culture solution thereof prepared according to the above-described method is for preparation of a cell therapy product, a pharmaceutical composition, or a preparation.

According to another aspect of the present disclosure, a method of treating a disease includes administering the mesenchymal stem cells, a population thereof, or a culture solution thereof prepared according to the above-described method into an individual in an effective amount.

According to the method of preparing mesenchymal stem cells according to an embodiment, a cell therapy product may be provided within a reduced period compared to that previously reported. Thus, the cell therapy product or the pharmaceutical composition may be obtained by subculturing for at least 3 passages, e.g., 3 passages to 10 passages, and differentiation of pluripotent stem cells may be induced and culturing may be performed for 20 days to 40 days, 22 days to 38 days, or 25 to 35 days for application as the cell therapy product. A culture period for application as the cell therapy product may refer to a differentiation period from pluripotent stem cells (Day 0) to a time in which the product is applicable as the cell therapy product.

According to another aspect of the present disclosure, a method of preparing a cell therapy product including mesenchymal stem cells includes subculturing the mesenchymal stem cell prepared according to the above-described method.

The subculturing is a process of culturing at least 3 passages, e.g., for 3 passages to 10 passages, and a period during which differentiation from pluripotent stem cells (Day 0) is induced and culturing is performed for application as the cell therapy product may be from 20 days to 40 days.

In addition, for example, a pharmaceutical composition for treating or preventing an inflammatory disease, an ischemic disease, and/or a neurodegenerative disorder includes mesenchymal stem cells, a population thereof, or a culture solution thereof prepared according to the above-described method, as an active ingredient.

In addition, for example, provided is a use of mesenchymal stem cells, a population thereof, or a culture solution thereof prepared according to the above-described method for preparation of a pharmaceutical composition for treating or preventing an inflammatory disease, an ischemic disease, and/or a neurodegenerative disorder.

According to another aspect of the present disclosure, a method of preventing or treating an inflammatory disease, an ischemic disease, and/or a neurodegenerative disorder includes administering mesenchymal stem cells, a population thereof, or a culture solution thereof prepared according to the above-described method to an individual in need thereof in an effective amount.

The mesenchymal stem cells prepared according to the above-described method are as described above.

Examples of the disease may include inflammatory diseases, ischemic diseases, and/or neurodegenerative disorders. Examples of the inflammatory diseases may include bronchitis, gastritis, arteriosclerosis, arthritis, inflammatory bowel disease (IBD), hepatitis, cholecystitis, fungal infections, gastric ulcers, asthma, atopic dermatitis, tendinitis, or nephritis. Examples of the ischemic diseases may include ischemic stroke, myocardial infarction, ischemic heart disease, ischemic brain syndrome, ischemic heart failure, ischemic enteritis, ischemic vascular disease, ischemic eye disease, ischemic retinopathy, ischemic glaucoma, ischemic renal failure, or ischemic lower limb disease.

Examples of the neurodegenerative disorders may include spinal cord injury, multiple sclerosis, Alzheimer's disease, frontotemporal dementia, progressive supranuclear palsy, corticobasal degeneration, Pick's disease, or dementia pugilistica (DP).

A dosage of the pharmaceutical composition or the cell therapy product according to an embodiment may be $1.0 \times 10^3$ to $1.0 \times 10^{10}$ cell/kg (body weight) or subject, or $1.0 \times 10^7$ to $1.0 \times 10^8$ cell/kg (body weight) or subject, based on mesenchymal stem cells. However, the dosage may be variously prescribed depending on various factors such as a formulation method, an administration mode, a patient's age, body weight, gender, severity of disease, diet, an administration time, an administration route, an excretion rate, and drug sensitivity, and those skilled in the art may appropriately adjust the dosage, in consideration of these factors. Administration frequency may be once or twice or more within the clinically allowable range of side effects, and administration may be given to one site or two or more sites. The dosage per kg or per subject for non-human animals may be the same as that for humans, or may be converted from the above-described dosage, for example, based on a volume ratio (e.g., average value) between organs (heart, etc.) of the human and animal subjects. Animals to be treated according to an embodiment may be exemplified by humans and other desired mammals, and specifically, may include humans, monkeys, mice, rats, rabbits, sheep, cows, dogs, horses, pigs, etc.

The cell therapy product or the pharmaceutical composition according to an embodiment may include the mesenchymal stem cells, as an active ingredient, and a pharmaceutically acceptable carrier and/or additive. For example, sterilized water, physiological saline, a standard buffer (e.g., phosphoric acid, citric acid, or other organic acids), a stabilizer, a salt, an antioxidant (e.g., ascorbic acid, etc.), a surfactant, a suspending agent, an isotonic agent, a preservative, or the like may be included therein. For topical administration, the cell therapy product or the pharmaceutical composition is preferably combined with an organic substance such as a biopolymer, an inorganic substance such as hydroxyapatite, specifically, collagen matrix, a polymer or copolymer of polylactic acid, a polymer or copolymer of polyethylene glycol, and chemical derivatives thereof. When the cell therapy product or the pharmaceutical composition according to an embodiment is prepared in an injectable formulation, cell populations may be dissolved in a pharmaceutically acceptable carrier or may be frozen in a solution state in which the cell populations are dissolved.

The mesenchymal stem cells according to an embodiment may be used in various types of therapeutic protocols in which tissue or an organ in a living body is enhanced, treated, or replaced by engraftment, transplantation, or infusion of target cell population, e.g., stem cells or derived cell population. Existing tissue may be replaced with or enhanced by the pluripotent stem cell-derived mesenchymal stem cells, to become new or changed tissue or to be combined with a biological tissue or structure.

The cell therapy product or the pharmaceutical composition according to an embodiment may include a suspending agent, a solubilizing aid, a stabilizer, an isotonic agent, a preservative, an adsorption inhibitor, a surfactant, a diluent, an excipient, a pH adjuster, an analgesic agent, a buffer, a reducing agent, an antioxidant, etc., if necessary depending upon the administration mode and formulation. In addition to those described above, pharmaceutically acceptable carriers and agents suitable in the present disclosure are described in detail in a document [Remington's Pharmaceutical Sciences, $19^{th}$ ed., 1995].

The cell therapy product or the pharmaceutical composition according to an embodiment may be formulated in a unit dosage form or into a multidose container using a pharmaceutically acceptable carrier and/or excipient according to a method that may be easily carried out by those skilled in the art to which the present disclosure pertains. In this regard, the formulation may be in a form of a solution, suspension, or emulsion in an oily or aqueous medium, a powder, granules, a tablet, or a capsule. Also, the cell therapy product may be formulated into an injectable form. In this case, any known components for formulation may be used and the cell therapy product may be formulated using any method well known in the art.

Advantageous Effects Of Disclosure

According to the medium composition and the method according to an embodiment, mesenchymal stem cells may be prepared at high yield within a short period of time. In addition, the method is simple in preparation procedure because of the absence of an embryoid body formation step and allows homogeneous cells to be prepared, thus advantageously providing a cell therapy product within a reduce period of time, compared to conventional methods.

MODE OF DISCLOSURE

Figure 1:
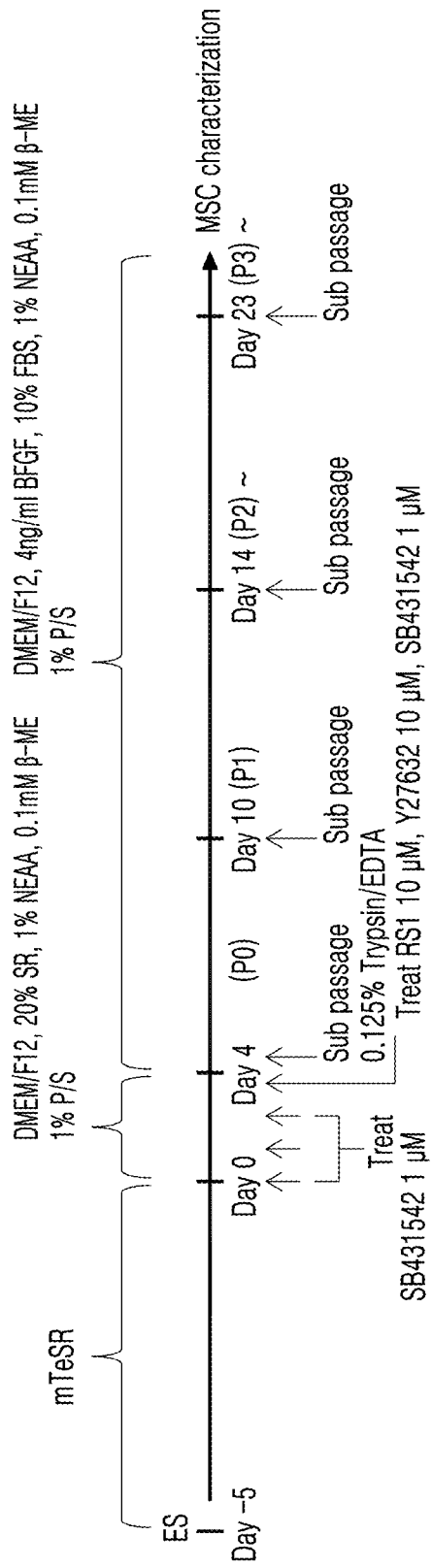
FIG. 1 is a schematic diagram of a method for direct differentiation of human embryonic stem cells into mesenchymal stem cells according to an embodiment.

Hereinafter, the present disclosure will be described in more detail with reference to the following examples. However, the following examples are merely presented to exemplify the present disclosure, and the scope of the present disclosure is not limited thereto.

Example 1. Direct Differentiation of Human Embryonic Stem Cell into Mesenchymal Stem Cell 1.1. Culture of Human Embryonic Stem Cell Human embryonic stem cells were cultured without feeder cells as follows.

Specifically, a 4-well tissue culture dish having a surface area of 2.0 cm$^2$ was treated with CTS Cellstart™, which is a cell adhesion enhance consisting of components derived only from humans in a concentration of 160 µl/well at 4° C. for 24 hours. Then, after all of CTS Cellstart™ remaining on the tissue culture dish was removed therefrom at room temperature, a mTeSR™ (StemCells, USA) medium, as an embryonic stem cell conditioned medium, was added to the tissue culture dish in a concentration of 500 µl/well, and then the tissue culture dish was placed in a 5% CO$_2$ incubator at 37° C.

Subsequently, human embryonic stem cells (CHA-hES NT 18, CHA university) proliferated on feeder cells were divided into small clumps using a Micro-tip (Axygen, USA) by mechanical sub-passage, and the clumps were seeded on the tissue culture dish placed in the incubator at a density of 15 to 20 clumps/well. Then, the human embryonic stem cells were proliferated without the feeder cells while replacing the medium with a fresh embryonic stem cell conditioned medium (mTeSR™) in a concentration of 500 µl/well every day for 5 days.

1.2. Induction of Differentiation of Human Embryonic Stem Cell into Mesodermal Cell The human embryonic stem cells proliferated without feeder cells in Example 1.1 were treated with a TGF-β inhibitor to be differentiated into mesodermal cells.

Specifically, the TGF-β inhibitor (SB431542) was dissolved in dimethylsulfoxide (DMSO, Sigma, USA) in a stock concentration of 1 mM and diluted in an embryonic stem cell differentiation medium (DMEM/F12, 20% (v/v) SR, 1% (v/v) NEAA, 0.1 mM β-mercaptoethanol, and 1% (v/v) penicillin-streptomycin) to a final concentration of 1 µM. Then, the human embryonic stem cells proliferated for 5 days according to Example 1.1 were treated in the embryonic stem cell differentiation medium containing SB431542 for 4 days (Day 0, 1, and 2) to be differentiated into mesodermal cells.

1.3. Pretreatment of Mesodermal Cell

In Example 1.2, the medium was replaced with a fresh medium on the 3$^{rd}$ day of treatment with the embryonic stem cell differentiation medium, and then the cells were further cultured for 1 day. Specifically, the mesodermal cells were pre-treated by replacing the medium with a differentiation medium containing a 10 µM Rad51 activator (RS1), a 10 µM ROCK inhibitor (Y27632), and a 1 µM TGF-β inhibitor (SB431542).

1.4. Induction of Differentiation into Mesenchymal Stem Cell

The mesodermal cells pre-treated in Example 1. 3 were differentiated into mesenchymal stem cells and subcultured to obtain mesodermal stem cells.

Specifically, all of the culture medium was removed on the 4$^{th}$ day of differentiation, and then the cells were washed with PBS mixed with 1% (v/v) penicillin-streptomycin. Then, the resultant was treated with 0.125% trypsin at room temperature to prepare a single cell suspension and neutralized with a mesenchymal stem cell maturation medium (DMEM/F12, 10% (v/v) FBS, 4 ng/ml bFGF, 1% (v/v) NEAA, 0.1 mM β-mercaptoethanol, and 1% (v/v) penicillin-streptomycin), and then centrifuged. Subsequently, the cells obtained by centrifuging were seeded on 1-well/12-well dishes coated with CTS Cellstart™ and continuously subcultured, in the order of 12-well dish (Passage 0)→6-well dish (Passage 1)→T-25 flask (Passage 2)→T-75 flask (Passage 3) whenever a cell confluency reached 80% to 90%, by a method of preparing a single cell suspension via treatment with 0.05% trypsin at room temperature. During this process, non-mesodermal stem cells were dropped and mesodermal stem cells were recovered.

A method of preparing mesenchymal stem cells according to an embodiment is schematically shown in FIG. 1.

Comparative Example 1 Preparation of Mesenchymal Stem Cell Via Embryoid Body-Forming System As a control, mesenchymal stem cells were prepared from human embryonic stem cells (hESCs) via an embryoid body-forming system. The mesenchymal stem cells were prepared via the embryoid body-forming system as follows.

Specifically, human embryonic stem cell lines were co-cultured in a colony form on MEF feeder cells previously prepared in a concentration of 7.5×10$^4$ cells/well (0.1% gelatin coated dish, 4 well). For formation of an embryoid body (EB), the hESCs were mechanically separated into several groups (2 to 4 clump forms) using a sterilized tip under a dissecting microscope and cultured for 5 days on a 60 mm Petri dish in a Dulbecco's Modified Eagle Medium; Nutrient Mixture F-12 (DMEM/F12) medium supplemented with 20% knockout-serum replacement (KSR, Invitrogen). After EB formation, the cells were cultured one day in a 20% KSR+DMEM/F12 medium (EB medium:medium excluding only bFGF from hESC medium), and then cultured for 2 weeks (13 days) in the EB medium after adding a 1 μM TGF-beta inhibitor (SB431542) thereto, and the medium was replaced once every two days. Then, the cells were transferred to a 6-well plate coated with 0.1% gelatin (30 min, air dry) such that a density of EB was 5 to 7 in one well and further cultured for 16 days in a DMEM (low glucose: 5.5 mM D-glucose (1 g/L)) supplemented with 10% FBS and 1% penicillin-streptomycin (P/S, Invitrogen). After 48 hours of culturing, adhesion of EB and cells extending out of the EB were identified, and the medium was replaced twice a week. After 16 days, the cells extending from the EB were separated using a TrypLE solution (Invitrogen; 500 μl TrypLE per 1 well, 2 min incubation), transferred to a 75T flask coated with 0.1% gelatin, and cultured in a DMEM (low glucose: 5.5 mM D-glucose (1 g/L)) supplemented with 10% FBS and 1% P/S. Next day, mesenchymal stem cells were prepared by subculturing in a DMEM (low glucose; 5.5 mM D-glucose (1 g/L) supplemented with 10% FBS, 1% P/S, and subculturing the cells in a MSC proliferation medium including 10% FBS, 1% P/S, 1% nonessential amino acids (NEAA, Invitrogen) and 0.1% 3-mercaptoethanol (Invitrogen) using 0.05% Trypsin-EDTA (1.5 ml per 75T flask, 2 min incubation) whenever a cell confluency is reached.

Comparative Example 2. Preparation of Mesenchymal Stem Cell by Treatment with DNA Repair Agent Alone Mesenchymal stem cells were prepared in the same manner as in Example 1, except that both the 10 μM Rad51 activator (RS1) and the 1 μM TGF-β inhibitor (SB431542) were used without using the ROCK inhibitor in Example 1.3.

Comparative Example 3. Preparation of Mesenchymal Stem Cell by Treatment with ROCK Inhibitor Alone Mesenchymal stem cells were prepared in the same manner as in Example 1, except that both the 10 μM ROCK inhibitor (Y27632) and the 1 μM TGF-β inhibitor (SB431542) were used without using the DNA repair agent in Example 1.3.

Experimental Example Analysis of Characteristics of Human Embryonic Stem Cell-derived Mesenchymal Stem Cell 1. Analysis of Cytomorphological Feature For analysis of cytomorphological features of mesenchymal stem cells obtained in Example 1 and Comparative Example 1, a mesenchymal stem cell-specific proliferation pattern (spindle shape) was identified under a phase-contrast microscope (Nikon TE-2000), and the results are shown in FIGS. 2 and 3, respectively.

Figure 2:
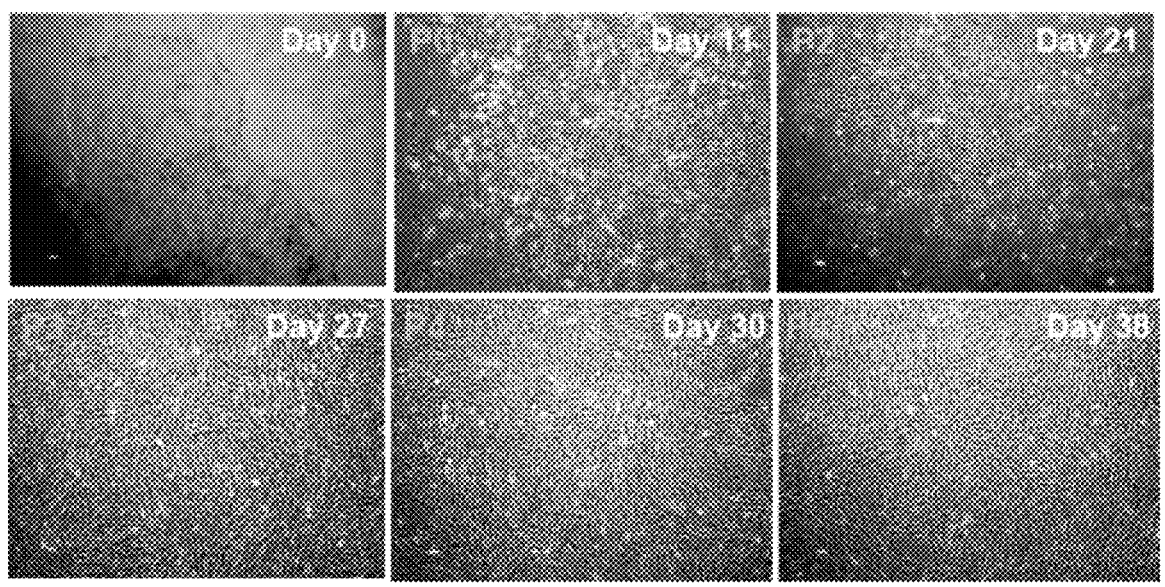
FIG. 2 shows photographs illustrating cytomorphological features of human embryonic stem cell-derived mesenchymal stem cells according to an embodiment.

FIG. 2 shows photographs illustrating cytomorphological features of human embryonic stem cell-derived mesenchymal stem cells according to an embodiment.

Figure 3:
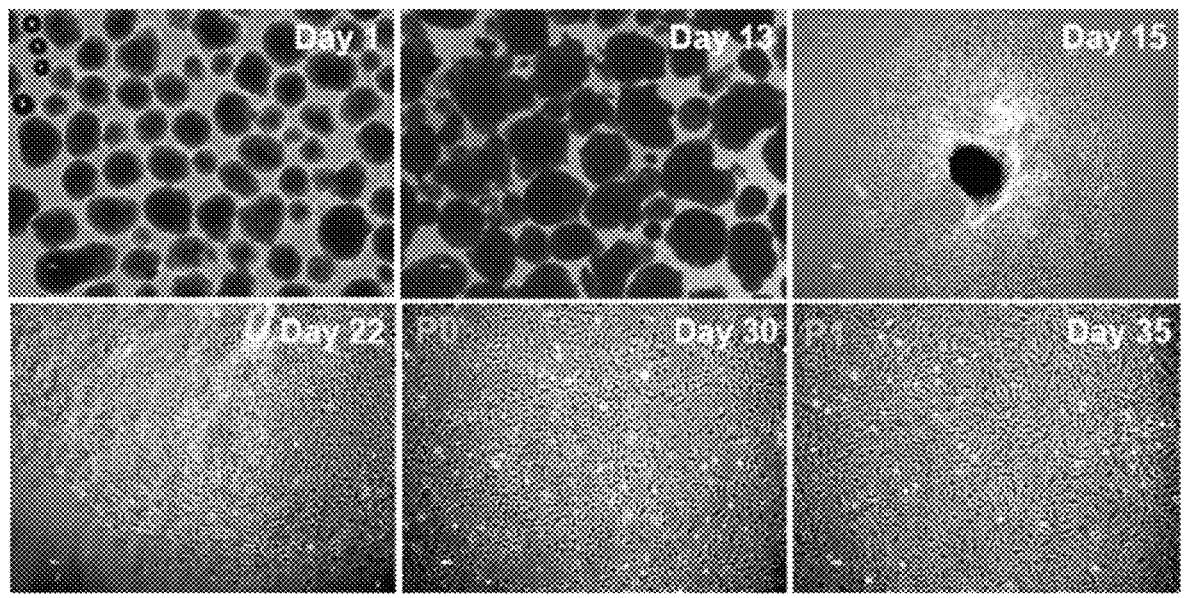
FIG. 3 shows photographs illustrating cytomorphological features of human embryonic stem cell-derived mesenchymal stem cells via an embryoid body-forming system according to a comparative example.

FIG. 3 shows photographs illustrating cytomorphological features of human embryonic stem cell-derived mesenchymal stem cells via an embryoid body-forming system according to Comparative Example 1.

As shown in FIG. 2, it was confirmed that the human embryonic stem cell-derived mesenchymal stem cells prepared according to the method according to an embodiment exhibited gradual proliferation in a spindle-like shape similar to that of adult tissue-derived mesenchymal stem cells about on the $10^{th}$ day from differentiation and most of the cells had the shape of the mesenchymal stem cells about on the $24^{th}$ day from differentiation. On the contrary, as shown in FIG. 3, it was confirmed that the human embryonic stem cell-derived mesenchymal stem cells prepared using the previously reported embryoid body-forming system exhibited proliferation in a spindle shape on the $40^{th}$ day.

These results indicate that cells having mesenchymal stem cell-specific shapes may be obtained at high yield within a shorter period of time according to the method according to an embodiment when compared with the previously reported method.

2. Cell Yield Analysis

The number of proliferating cells were identified to analyze the yield of cells obtained according to the method of Example 1. Specifically, in the process of preparing mesenchymal stem cells according to Example 1 and Comparative Example 1, the cells were stained with a 0.4% (v/v) trypan blue solution in the preparing of the single cell suspension. Then, the number of viable cells was analyzed using a hemocytometer, and the results are shown in FIG. 4.

In addition, in view of cytomorphological features of Example 1.4, an appropriate time in which the human embryonic stem cell-derived mesenchymal stem cells prepared according to the method of according to an embodiment were applicable as a cell therapy product was 3 passages or more where the mesenchymal stem cell-specific shape, i.e., the spindle shape, was observed. Thus, differentiation time of human embryonic stem cell-derived mesenchymal stem cell lines suitable for application to cell therapy was analyzed in the same manner, and the results are shown in FIG. 5.

Figure 4:
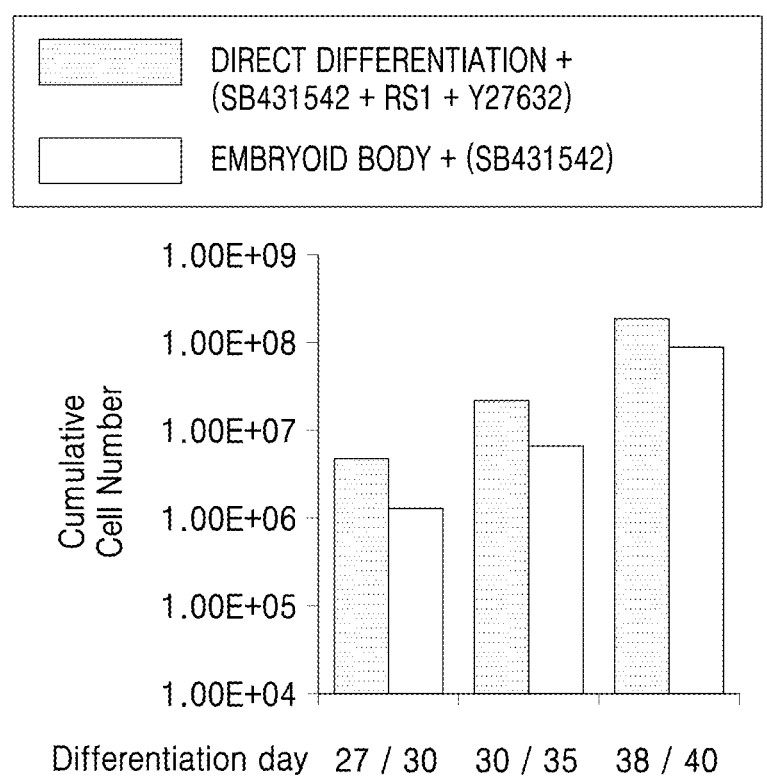
FIG. 4 is a graph illustrating comparison results between yields of human embryonic stem cell-derived mesenchymal stem cells according to an embodiment (direct differentiation+SB431542+RS1+Y27632) and yields of human embryonic stem cell-derived mesenchymal stem cells prepared using an embryoid body-forming system (differentiation via an embryoid body+SB431542).

FIG. 4 is a graph illustrating comparison results between yields of human embryonic stem cell-derived mesenchymal stem cells according to an embodiment (direct differentiation+SB431542+RS1+Y27632) and yields of human embryonic stem cell-derived mesenchymal stem cells prepared using an embryoid body-forming system (embryoid body+SB431542).

Figure 5:
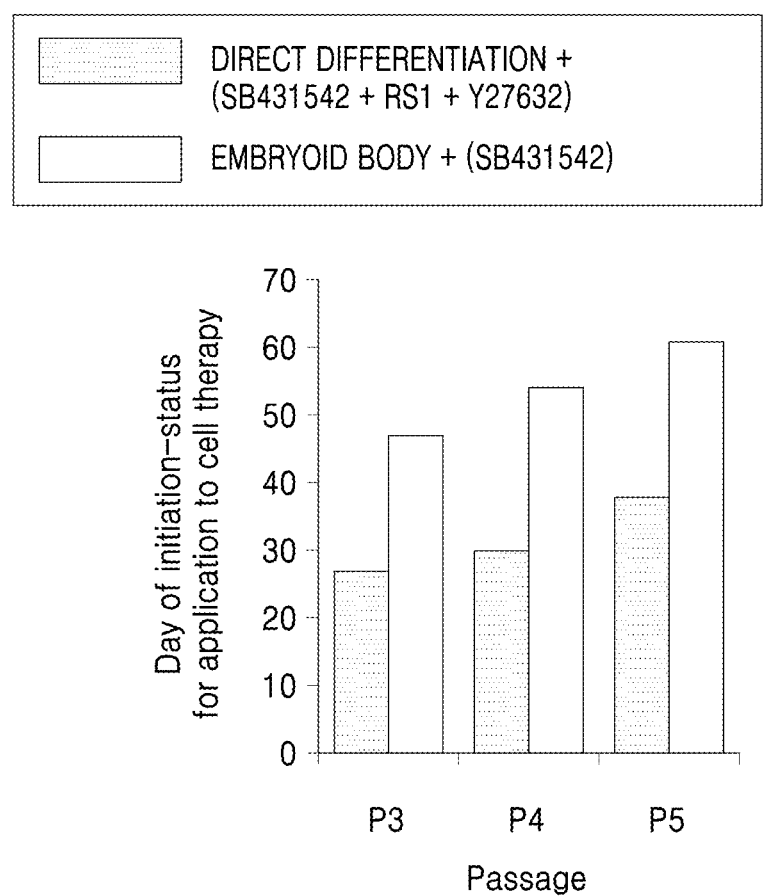
FIG. 5 is a graph illustrating comparison results between differentiation periods of human embryonic stem cell-derived mesenchymal stem cells according to an embodiment (direct differentiation+(SB431542+RS1+Y27632)) required to be applied as a cell therapy product and differentiation periods of human embryonic stem cell-derived mesenchymal stem cells prepared using an embryoid body-forming system (an embryoid body+SB431542)).

FIG. 5 is a graph illustrating comparison results between differentiation periods of human embryonic stem cell-derived mesenchymal stem cells according to an embodiment (direct differentiation+(SB431542+RS1+Y27632)) required to be applied as a cell therapy product and differentiation periods of human embryonic stem cell-derived mesenchymal stem cells prepared using an embryoid body-forming system (embryoid body+SB431542)).

As shown in FIG. 4, it was confirmed that a large number of cells may be obtained within a short period of time compared to the previously reported method according to the method of preparing human embryonic stem cell-derived mesenchymal stem cells according to an embodiment.

Also, as shown in FIG. 5, it was confirmed that the differentiation period enough to be applied as a cell therapy product according to the method according to an embodiment may be shortened by about 1.5 times to twice compared to the previously reported embryoid body formation system.

3. Analysis of Surface Expression Marker

For analysis of surface expression markers of the human embryonic stem cell-derived mesenchymal stem cells prepared in Example 1, flow cytometry was performed.

Specifically, the human embryonic stem cell-derived mesenchymal stem cells (on the 30$^{th}$ day of culturing (Passage 4)) were washed with PBS supplemented with 1% (v/v) penicillin-streptomycin and then a single cell suspension was prepared using trypsin (0.05%, Trypsin/EDTA, Gibco, USA). Subsequently, the cells were immobilized with a cold 4% formaldehyde solution at room temperature for 30 minutes and washed four times with PBS supplemented with 0.2% (v/v) FBS. Subsequently, APC- or PE-labeled antibody was diluted with PBS supplemented with 0.2% FBS to a final concentration of 5 μg to 15 μg and maintained under dark conditions for 30 minutes at room temperature. Then, the resultant was washed four times with PBS supplemented with 0.2% (v/v) FBS and then expression levels were analyzed by a flow cytometer. As antibodies, antibodies to a pluripotent marker TRA-1-60 (phycoerythrin (PE)-conjugated mouse anti-human TRA-1-60; Cat. 560193, BD Pharmingen™), a hematopoietic stem cell marker CD34 (allophycocyanine (APC)-conjugated mouse anti-human CD34; Cat. 555824, BD Pharmingen™), a hemangioblast marker VEGFR2 (APC-conjugated mouse anti-human VEGFR2; Cat. BD Pharmingen™), and mesenchymal stem cell markers CD29 (APC-conjugated mouse anti-human CD29; Cat. 559883, BD Pharmingen™) CD44 (APC-conjugated mouse anti-human CD44; Cat. 559942, BD Pharmingen™) CD90 (APC-conjugated mouse anti-human CD90; Cat. 561971, BD Pharmingen™), and CD105 (APC-conjugated mouse anti-human CD105; Cat. 562408, BD Pharmingen™) were used.

Figure 6:
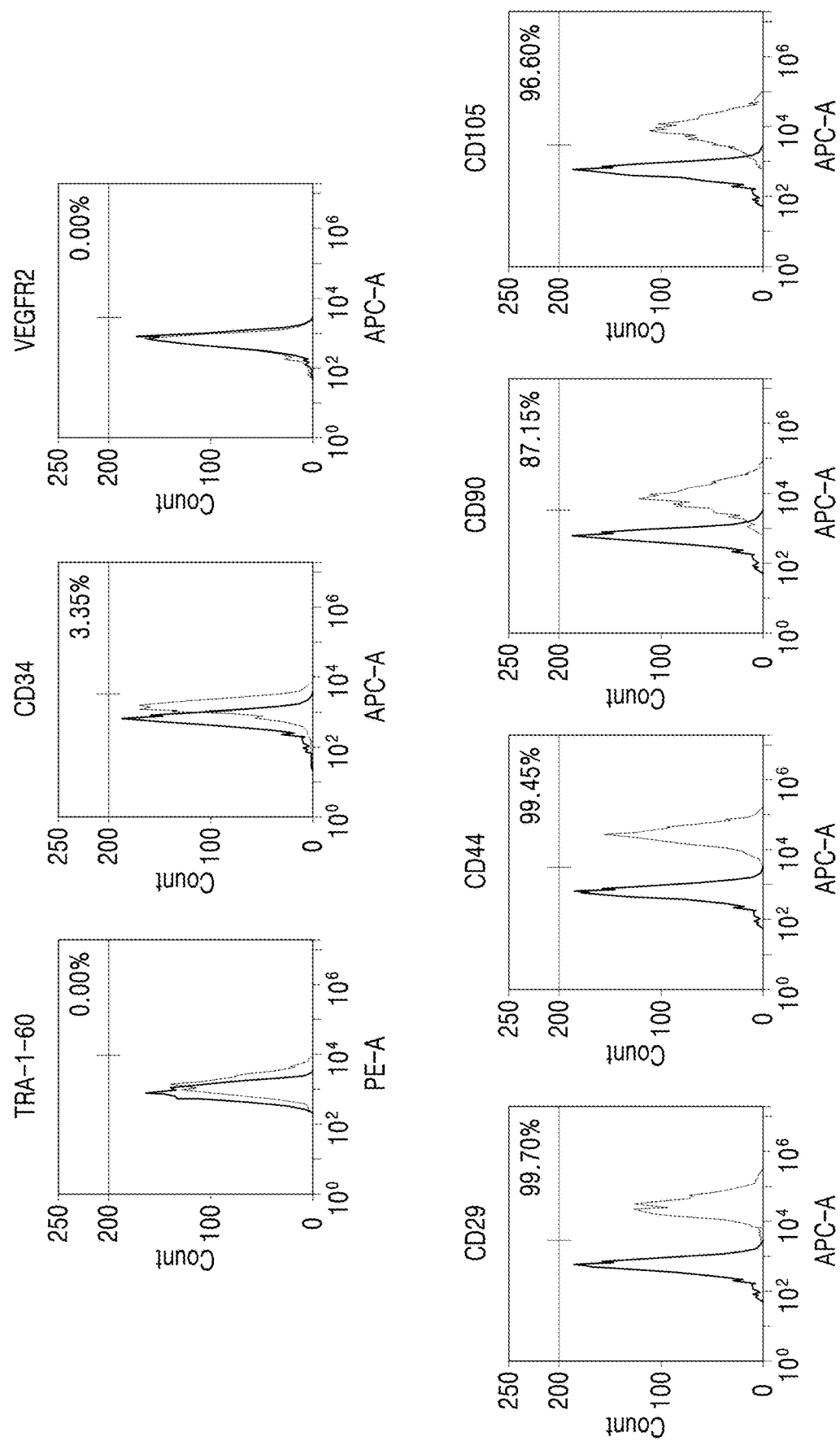
FIG. 6 shows analysis results of cell surface expression markers of human embryonic stem cell-derived mesenchymal stem cells on the 30$^{th}$ day of culturing (Passage 4) by flow cytometry.

The results of flow cytometry are shown in FIG. 6.

Figure 7:
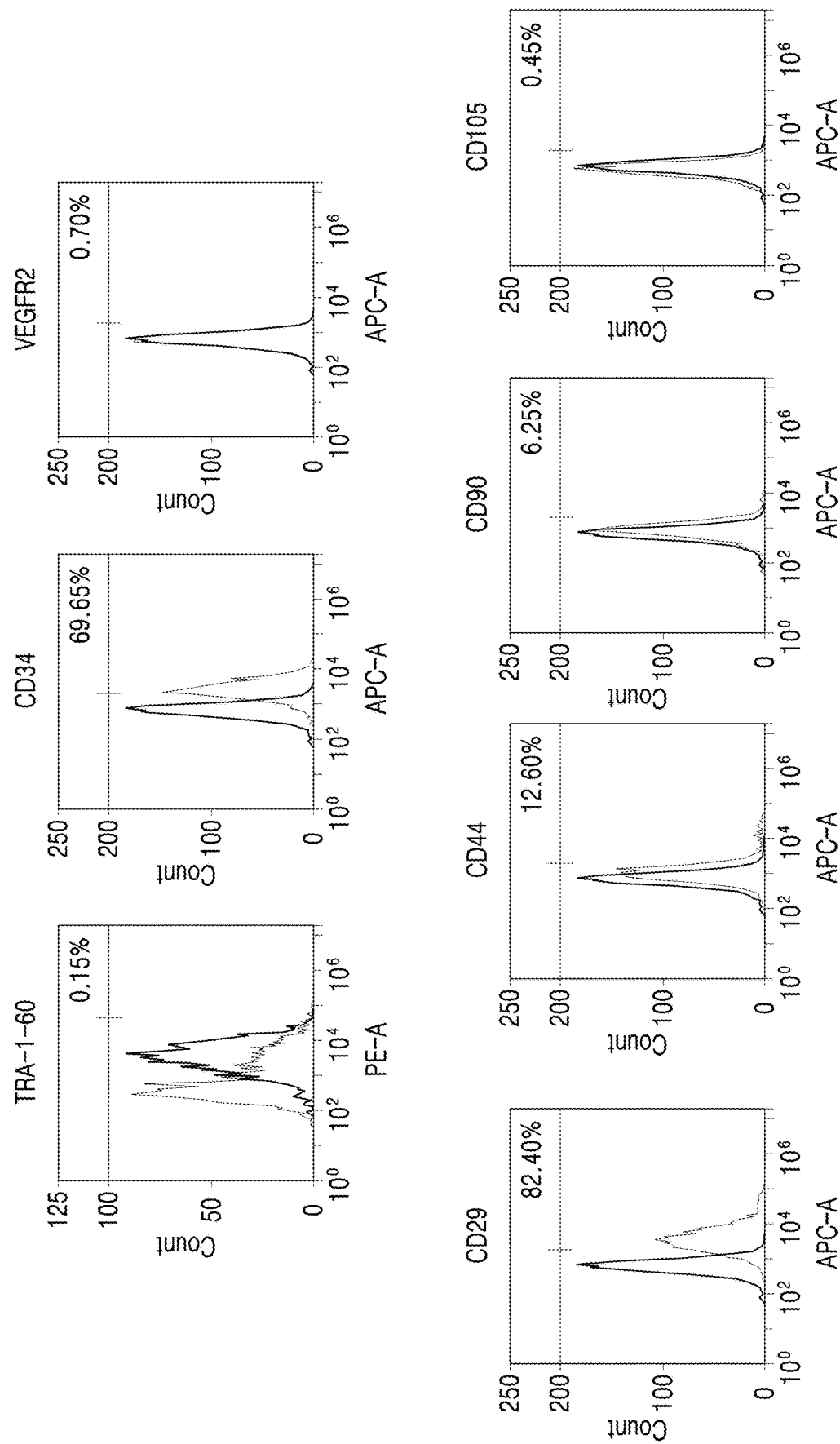
FIG. 7 shows analysis results of cell surface expression markers of human embryonic stem cell-derived mesenchymal stem cells on the 4$^{th}$ day of culturing by flow cytometry.

In addition, to identify whether differentiation according to an embodiment occurs without forming hemangioblasts, expression of surface markers of the cells (Example 1.3) was analyzed on the 4$^{th}$ day of culturing by flow cytometry, and the results are shown in FIG. 7.

Figure 8:
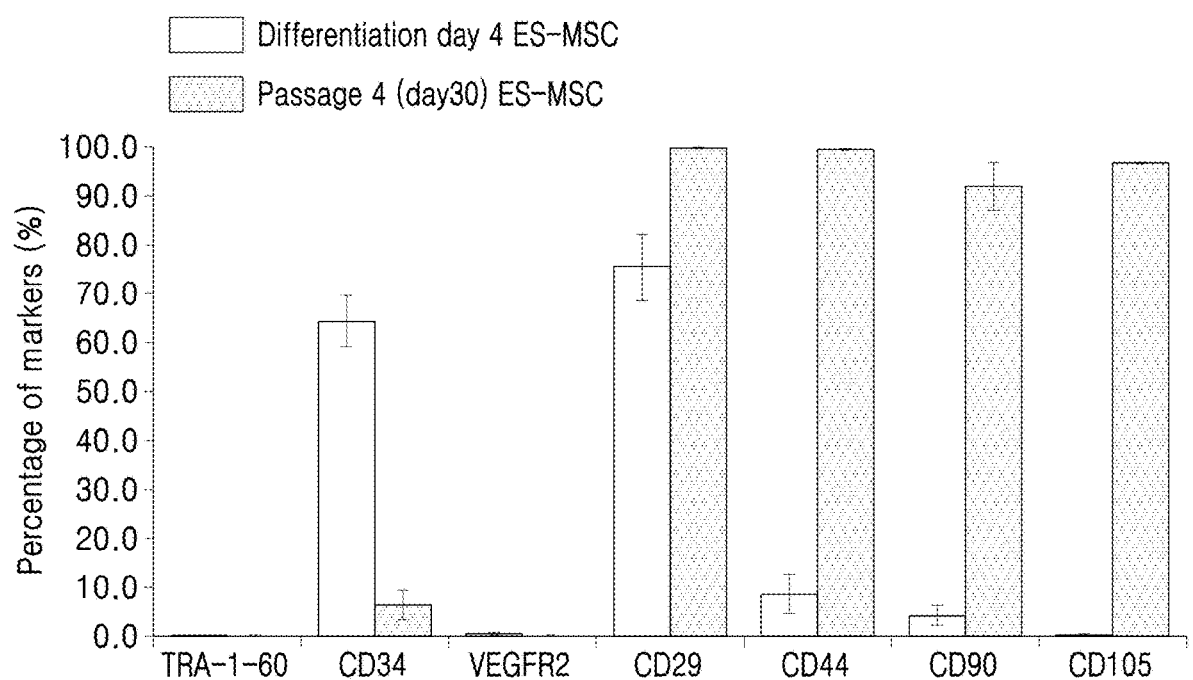
FIG. 8 is a graph illustrating comparison results between cell surface expression markers of human embryonic stem cell-derived mesenchymal stem cells according to an embodiment on the 30$^{th}$ day of culturing (Passage 4) and on the 4$^{th}$ day of culture.

In addition, analysis results of expression of surface markers of the cells on the 30$^{th}$ day of culturing (Passage 4) were compared and the results are shown in FIG. 8.

FIG. 6 shows analysis results of cell surface expression markers of human embryonic stem cell-derived mesenchymal stem cells on the 30$^{th}$ day of culturing (Passage 4) by flow cytometry.

FIG. 7 shows analysis results of cell surface expression markers of human embryonic stem cell-derived mesenchymal stem cells on the 4$^{th}$ day of culturing by flow cytometry.

FIG. 8 is a graph illustrating comparison results between cell surface expression markers of human embryonic stem cell-derived mesenchymal stem cells according to an embodiment on the 30$^{th}$ day of culturing (Passage 4) and on the 4$^{th}$ day of culture.

As shown in FIG. 6, as a result of identifying expression of the pluripotent marker TRA-1-60, the hematopoietic stem cell marker CD34, and the mesenchymal stem cell markers CD29, CD44, CD90, and CD105 in the human embryonic stem cell-derived mesenchymal stem cells according to an embodiment, it was confirmed that the pluripotent marker TRA-1-60 was not expressed (TRA-1-60: 0.00%), but the mesenchymal stem cell markers were expressed at high rates (CD29: 99.70%; CD44: 99.45%; CD90: 87.15%; and CD105: 96.60%). Therefore, it was confirmed that the human embryonic stem cell-derived mesenchymal stem cells induced by the method according to an embodiment have high mesodermal properties.

In addition, as shown in FIG. 7, as a result of analyzing surface markers of the cells on the 4$^{th}$ day of differentiation, it was confirmed that the hematopoietic stem cell marker CD34 was expressed at a high rate (CD34: 69.65%), but the hemangioblast marker VEGFR2 was hardly expressed (VEGFR2: 0.70%).

In addition, as shown in FIG. 8 indicating a comprehensive result of those of FIGS. 6 and 7, it was confirmed that the mesenchymal stem cell markers were expressed at high rates on the 30$^{th}$ day (Passage 4) of differentiation, the hematopoietic stem cell marker CD34 was expressed at a high rate and the hemangioblast marker VEGFR2 was expressed at a low rate on the 4$^{th}$ day of differentiation.

These results indicate that mesenchymal stem cells were prepared via immature mesenchymal stem cells having characteristics of hematopoietic stem cells without forming hemangioblasts according to the method of preparing human embryonic stem cell-derived mesenchymal stem cells according to an embodiment.

4. Analysis of Cell Differentiation Ability

The differentiation ability of human embryonic stem cell-derived mesenchymal stem cells prepared in Example 1 into adipocytes, osteocytes, and chondrocytes were identified.

Specifically, differentiation was induced into adipocytes, osteocytes, and chondrocytes using an adipocyte differentiation inducer (StemPro®Adipocyte differentiation kit, Gibco), an osteocyte differentiation inducer (StemPro®Osteocyte differentiation kit, Gibco), and a chondrocyte differentiation inducer (StemPro®Chondrocyte differentiation kit, Gibco), respectively, in accordance with manufacturer's instructions. Cell differentiation was finally identified using staining solutions specific to adipocytes, osteocytes, and chondrocytes (Oil red O, Alizarin red, and Alcian blue, respectively), and the results are shown in FIG. 9.

Figure 9:
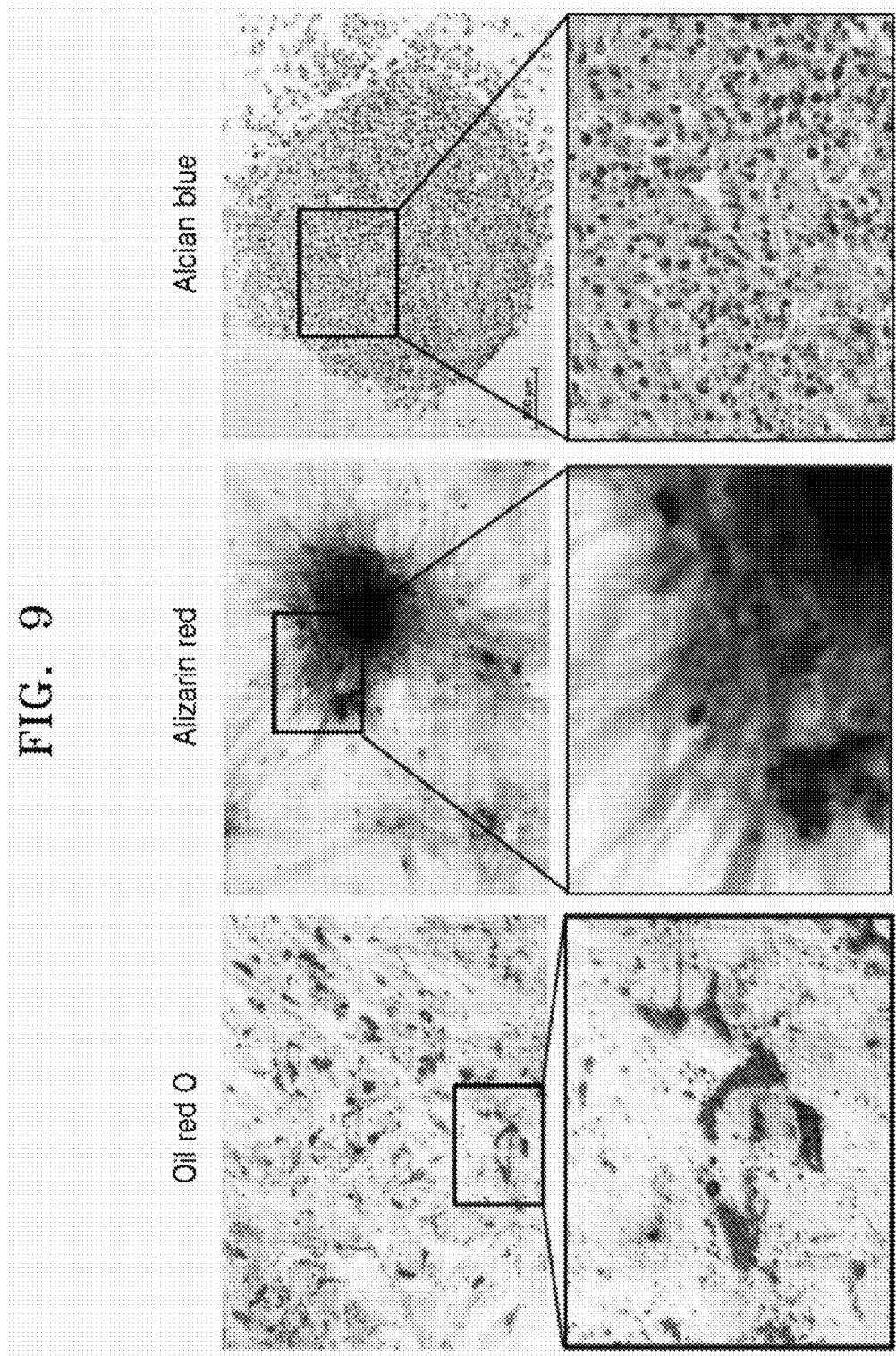
FIG. 9 is photographs showing differentiation ability of human embryonic stem cell-derived mesenchymal stem cells according to an embodiment.

FIG. 9 is photographs showing differentiation ability of human embryonic stem cell-derived mesenchymal stem cells according to an embodiment.

As shown in FIG. 9, in the case of inducing differentiation into adipocytes, lipid droplets stained in red were observed since lipid components in cells were stained by a lipid-specific staining solution Oil red O. In the case of inducing differentiation into osteocytes, a dark orange color was observed since calcium accumulated in cells was stained by the Alizarin red solution. In the case of inducing differentiation into chondrocytes, a blue color was observed since mucin that is an extracellular matrix of chondrocytes was stained by the chondrocyte-specific staining solution Alcian blue. As a result, it may be confirmed that the mesenchymal stem cells prepared according to an embodiment have multipotency capable of differentiating into adipocytes, osteocytes, and chondrocytes.

5. Analysis of Cytomorphological Difference by Period According to Treatment with Single Substance For analysis of cytomorphological difference by treatment with the DNA repair agent or the ROCK inhibitor alone on the basis of period, morphologies of cells of Example 1 and Comparative Examples 2 and 3 were analyzed in the same manner as in Experimental Example 1. As a control, cells treated with the TGF-β inhibitor SB431542 alone without being treated with both the DNA repair agent and the ROCK inhibitor were used, and the results are shown in FIG. 10.

Figure 10:
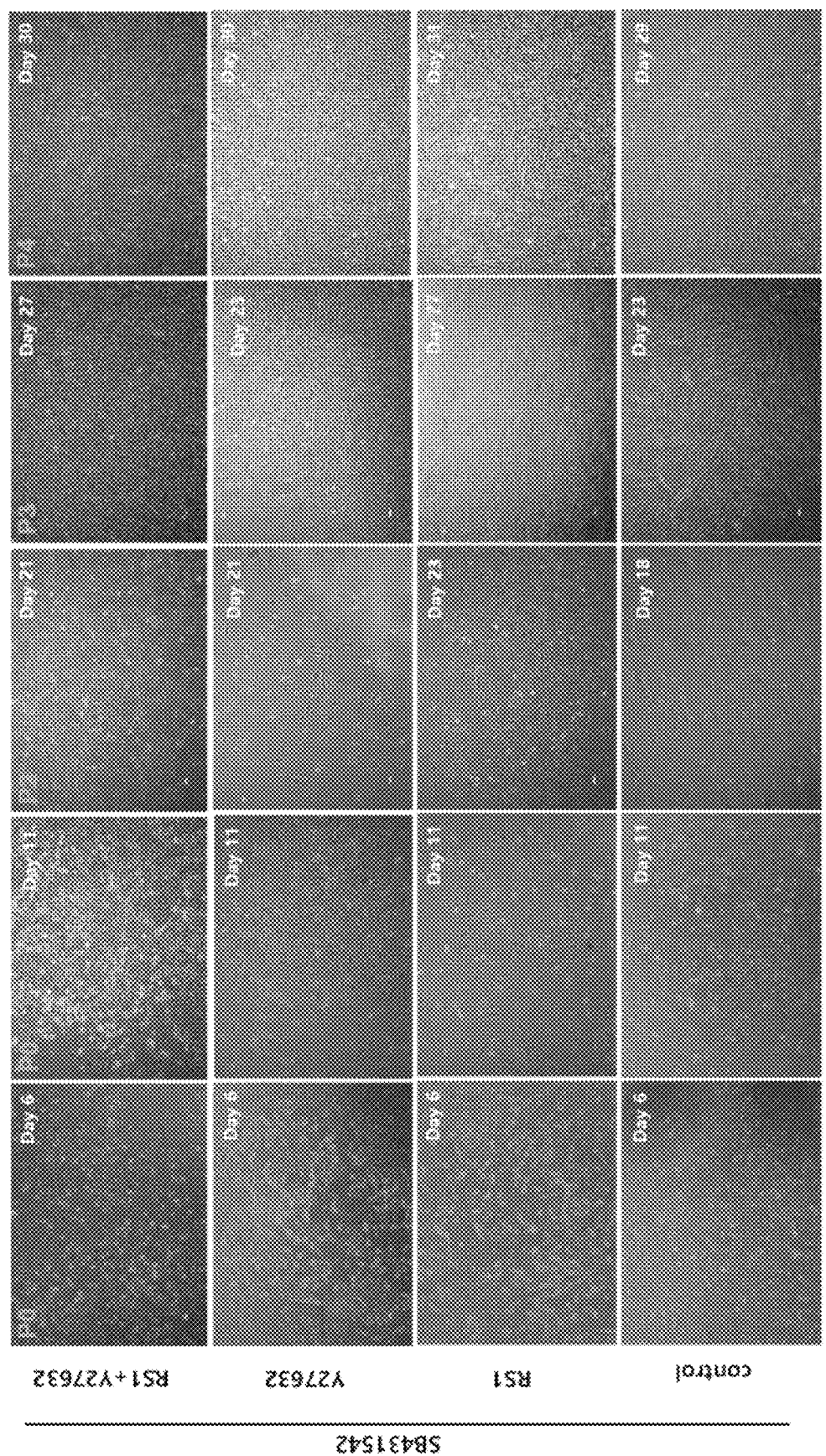
FIG. 10 shows photographs illustrating comparison results between cytomorphological features of human embryonic stem cell-derived mesenchymal stem cells according to an embodiment and cytomorphological features of human embryonic stem cell-derived mesenchymal stem cells prepared by treatment with a DNA repair agent or a ROCK inhibitor.

FIG. 10 shows photographs illustrating comparison results between cytomorphological features of human embryonic stem cell-derived mesenchymal stem cells according to an embodiment and cytomorphological features of human embryonic stem cell-derived mesenchymal stem cells prepared by treatment with a DNA repair agent or a ROCK inhibitor.

As shown in FIG. 10, although the mesenchymal stem cell proliferation pattern of the spindle shape was observed in all groups, the mesenchymal stem cells according to an embodiment (SB431542+RS1+Y27632) exhibited a high yield with the spindle shape first. In addition, uniform proliferation into mesenchymal stem cells was observed after about the 30$^{th}$ day when treated with SB431542+ Y27632 or SB431542+RS1. In the control treated with SB431542 alone, large-sized cells were observed about on the 23$^{rd}$ day, but most of the cells disappeared on the 30$^{th}$ day and uniformity deteriorated although cells in the form of mesenchymal stem cells similar to other groups were observed.

Based on the above-described results, it was confirmed that mesenchymal stem cells may be prepared at high yield within a short period of time according to the method of preparing mesenchymal stem cells according to an embodiment, and the method is simple in preparation procedure because of the absence of an embryoid body formation step and allows homogeneous cells to be prepared, thus advantageously providing a cell therapy product within a reduce period of time, compared to conventional methods.

The invention claimed is:

1. A method of preparing pluripotent stem cell-derived mesenchymal stem cells, the method comprising:
   (1) culturing isolated pluripotent stem cells; and
   (2) inducing differentiation of the cultured pluripotent stem cells into mesenchymal stem cells by culturing the pluripotent stem cells in a medium comprising a Rad51 activator and a Rho-associated, coiled-coil containing protein kinase (ROCK) inhibitor.

2. The method of claim 1, wherein the (2) inducing differentiation of the cultured pluripotent stem cells into mesenchymal stem cells further comprises: treating the cultured isolated pluripotent stem cells with a TGFβ-inhibitor; before culturing the treated cells in a medium comprising a Rad51 activator and a ROCK inhibitor.

3. The method of claim 1, wherein the culturing of isolated pluripotent stem cells is performed in a culture dish coated with a cell adhesion enhancer in the absence of feeder cells.

4. The method of claim 1, wherein the method does not comprise a process of forming an embryoid body.

5. The method of claim 1, wherein the Rad51 activator is 4-bromo-N-(4-bromophenyl)-3-[[(phenylmethyl)amino] sulfonyl]-benzamide.

6. The method of claim 1, wherein the ROCK inhibitor is one selected from Fasudil, Ripasudil, 4-((R)-1-aminoethyl)-N-(pyridin-4-yl)cyclohexanecarboxamide, 4-(1-aminoethyl)-N-(1H-pyrrolo (2,3-b)pyridin-4-yl)cyclohexanecarboxamide dihydrochloride, N-(6-fluoro-1H-indazol-5-yl)-1, 4,5,6-tetrahydro-2-methyl-6-oxo-4-[4-(trifluoromethyl) phenyl]-3-pyridinecarboxamide, 1-(3-hydroxybenzyl)-3-[4-(pyridin-4-yl) thiazol-2-yl]urea, 2-methyl-1-[(4-methyl-5-isoquinolinyl) sulfonyl]-hexahydro-1H-1,4-diazepine dihydrochloride, N-[2-[2-(dimethylamino) ethoxy]-4-(1H-pyrazol-4-yl)phenyl]-2,3-dihydro-1,4-benzodioxin-2-carboxamide dihydrochloride], 2-fluoro-N-[[4-(1H-pyrrolo[2, 3-b]pyridin-4-yl)phenyl]methyl]benzenemethanamine dihydrochloride, N-[3-[[2-(4-amino-1,2,5-oxadiazol-3-yl)-1-ethyl-1H-imidazo[4,5-c]pyridin-6-yl]oxy]phenyl]-4-[2-(4-morpholinyl)ethoxy]benzamide, (3S)-1-[[2-(4-amino-1, 2,5-oxadiazol-3-yl)-1-ethyl-1H-imidazo[4,5-c]pyridin-7-yl] carbonyl]-3-pyrrolidinamine dihydrochloride, N-[(1S)-2-hydroxy-1-phenylethyl]-N'-[4-(4-pyridinyl)phenyl]-urea, Azaindole-1, and Narciclasine.

7. The method of claim 1, wherein the medium further comprises a TGF-β inhibitor, and wherein culturing the pluripotent stem cells in the medium is performed for 1 day to 2 days.

8. The method of claim 1, wherein the pluripotent stem cells are nuclear transfer pluripotent stem cells (NT-hPSC), parthenote-derived human pluripotent stem cells (pn-hPSC), induced pluripotent stem cells (iPSC), or embryonic stem cells (ESC).

9. The method of claim 1, wherein the differentiation occurs not via hemangioblasts.

10. The method of claim 1, wherein the mesenchymal stem cells have the ability to differentiate into at least one selected from the group consisting of hematopoietic stem cells, myocytes, cardiomyocytes, hepatocytes, chondrocytes, epithelial cells, urinary cells, renal cells, vascular cells, retinal cells, and neuronal cells.

11. The method of claim 1, wherein the medium further comprises a TGF-β inhibitor.

12. The method of claim 11, wherein the TGF-β inhibitor is one selected from 4-{4-[3-(pyridin-2-yl)-1H-pyrazol-4-yl]-pyridin-2-yl}-N-(tetrahydro-2H-pyran-4-yl)benzamide hydrate, 4-[3-(2-pyridinyl)-1H-pyrazol-4-yl]-quinoline, 2-[3-(6-methyl-2-pyridinyl)-1H-pyrazol-4-yl]-1,5-naphthyridine, 4-[4-(1,3-benzodioxol-5-yl)-5-(2-pyridinyl)-1H-imidazol-2-yl]-benzamide hydrate, 3-(6-methyl-2-pyridinyl)-N-phenyl-4-(4-quinolinyl)-1H-pyrazole-1-carbothioamide, 2-(3-(6-methylpyridine-2-yl)-1H-pyrazol-4-yl)-1,5-naphthyridine, 4-[3-(2-pyridinyl)-1H-pyrazol-4-yl]-quinoline, 2-[4-(1,3-benzodioxol-5-yl)-2-(1,1-dimethylethyl)-1H-imidazol-5-yl]-6-methyl-pyridine, 2-(5-chloro-2-fluorophenyl)-4-[(4-pyridyl)amino]pteridine, 6-[2-tert-butyl-5-(6-methyl-pyridin-2-yl)-1H-imidazol-4-yl]-quinoxaline, 4-{4-[3-(pyridin-2-yl)-1H-pyrazol-4-yl]-pyridin-2-yl}-N-(tetrahydro-2H-pyran-4-yl)benzamide hydrate, 4-[2-fluoro-5-[3-(6-methyl-2-pyridinyl)-1H-pyrazol-4-yl]phenyl]-1H-pyrazole-1-ethanol, and 3-[[5-(6-methyl-2-pyridinyl)-4-(6-quinoxalinyl)-1H-imidazol-2-yl]methyl]benzamide.

13. The method of claim 2, wherein the treating the cultured isolated pluripotent stems cells with a TGF-β inhibitor comprises culturing the cells in a medium containing the TGF-β inhibitor for 2 days to 7 days.

* * * * *